US00PP17207P2

(12) United States Plant Patent
Cawthon

(10) Patent No.: US PP17,207 P2
(45) Date of Patent: Nov. 14, 2006

(54) ***LANTANA* PLANT NAMED 'WHITE GOLD'**

(50) Latin Name: *Lantana camara*
Varietal Denomination: WHITE GOLD

(76) Inventor: Noel Cawthon, 1011 Haynie Rd., Moreland, GA (US) 30259

( * ) Notice: Subject to any disclaimer, the term of this patent is extended or adjusted under 35 U.S.C. 154(b) by 0 days.

(21) Appl. No.: 11/123,909

(22) Filed: May 6, 2005

(51) Int. Cl.
*A01H 5/00* (2006.01)

(52) U.S. Cl. ..... Plt./227

(58) Field of Classification Search ..... Plt./227
See application file for complete search history.

*Primary Examiner*—Kent Bell

(57) ABSTRACT

A new variety of *Lantana* named 'WHITE GOLD' that is characterized by mounding spreading habit, medium-green colored foliage, and inflorescence that is predominantly white composed of pure-white florets with yellow eyes. In combination these traits set 'WHITE GOLD' apart from all other existing varieties of *Lantana* known to the inventor.

3 Drawing Sheets

Genus: *Lantana. Species: camara.*
Denomination: 'WHITE GOLD'.

BACKGROUND OF THE INVENTION

The present invention relates to a new and distinct cultivar of *Lantana* that is grown for its predominantly white inflorescence composed of pure-white florets with yellow eyes. The new cultivar is known botanically as *Lantana camara* and will be referred to hereinafter by the cultivar name 'WHITE GOLD'.

The inventor discovered and selected 'WHITE GOLD' in August 2004 at his nursery in Newnan, Ga. in the United States. 'WHITE GOLD' was discovered as a naturally occurring branch sport on an individual plant of *Lantana* 'New Gold' (unpatented). Selection was based on the criteria of inflorescence color.

When compared with *Lantana* 'New Gold', the new variety 'WHITE GOLD' exhibits identical habit, growth rate, and flower characteristics with the single distinguishing difference being the color of the inflorescence. The inflorescence of *Lantana* 'New Gold' is solid pure-yellow, whereas the inflorescence of 'WHITE GOLD' is predominantly white, being composed of pure-white florets with yellow eyes.

*Lantana* 'New Gold' has won many awards for its garden and landscape performance, due to the absence of seed set, and therefore absence of berry production. The berries of *Lantana* are highly poisonous. 'New Gold' is highly floriferous, due to its sterility. No seed or fruit has been produced to date by the new cultivar 'WHITE GOLD'.

The inventor has grown crops of the parent plant *Lantana camara* 'New Gold' since 1990. Each year, the inventor sets up fresh stock of 'New Gold' mother plants in order to produce cuttings for the following season's commercial crop. In 2003 the inventor purchased three thousand cuttings of 'New Gold' specifically for the 2004–2005 season. These cuttings were stuck into propagation plugs. Once rooted, three plugs were potted into 2-liter containers, which served as stock plants for that current year's propagation cycles. Thus, by spring 2004 the inventor possessed approximately one thousand stock plants, each grown from these individual cuttings.

Because *Lantana* cuttings root and grow rapidly, the inventor was able to take the first three thousand cuttings, as tip cuttings, within one month. By summer 2004 the inventor had used the stock plants for a total of four propagation cycles and had rooted and grown approximately thirty thousand plants.

*Lantana* blooms in the southern region of the United States within three to four weeks of rooting. During spring and summer 2004 the inventor observed that all of the plants grown from the harvested cuttings described above, flowered true to type for *Lantana* 'New Gold'—that is, they all bore solid pure-yellow flowers. In August 2004, the inventor observed that one single plant, which had been grown from the fourth cycle of cuttings, bore an inflorescence, which appeared predominantly white in color. The inventor removed and isolated this one plant and potted it into a 2-liter stockpot. The inventor considers this one plant, which is a naturally occurring white-flowering branch sport of *Lantana* 'New Gold', to be new and distinct, and the subject of the present invention *Lantana* plant named 'WHITE GOLD'. The inventor has found no evidence of a similar white flowered form in commerce.

The first asexual reproduction of 'WHITE GOLD' was conducted by the inventor in 2004 at the inventor's nursery in Newnan, Ga. in the United States. The method used for asexual propagation was shoot cuttings taken from the single plant discovered by the inventor. All plants thus propagated bore the same inflorescence as the original single plant of 'WHITE GOLD'—that is, predominantly white, composed of pure-white florets with yellow eyes. From fall 2004 until March 2005, the inventor has repeatedly asexually propagated 'WHITE GOLD' and has observed that all the plants have grown and flowered identically. Thus the inventor has determined that the characteristics herein described, of the new *Lantana* cultivar 'WHITE GOLD' are fixed, stable, and reproduce true to type in successive generations.

The cultivar considered by the inventor to be most similar to WHITE GOLD in habit is the parent variety *Lantana* 'New Gold' which appears to be identical in all respects except for the color of the inflorescence. The color of the inflorescence of *Lantana* 'New Gold' is orange-yellow, closest to the color reference 23A of The Royal Horticultural Society's Colour Chart, whereas the color of the inflorescence of 'WHITE GOLD' is predominantly pure white, as further described within the detailed botanical description.

The cultivar considered by the inventor to be most similar to WHITE GOLD in the color of its inflorescence is the unrelated variety *Lantana* 'Silver Mound' (unpatented). Whereas the flowers of 'WHITE GOLD' open with a clear white coloration and remain clear white (apart from the yellow center), the flowers of *Lantana* 'Silver Mound' open with a buttery-yellow coloration, and remain that color. In the landscape, the overall effect of 'WHITE GOLD' is of a much brighter, clearer white flowering display than is produced by *Lantana* 'Silver Mound'.

SUMMARY OF THE INVENTION

The following traits have been repeatedly observed and represent the characteristics of the new *Lantana* cultivar 'WHITE GOLD'. These traits in combination distinguish 'WHITE GOLD' from all other commercial varieties known to the inventor. 'WHITE GOLD' has not been tested under all possible conditions and phenotypic differences may be observed with variations in environmental, climatic and cultural conditions.

1. The inflorescence of *Lantana camara* 'WHITE GOLD' is predominantly white, being composed of pure-white florets with yellow eyes.
2. *Lantana camara* 'WHITE GOLD' exhibits mounding spreading habit.
3. *Lantana camara* 'WHITE GOLD' exhibits medium-green foliage.
4. *Lantana camara* 'WHITE GOLD' blooms from spring through fall.
5. The cultural requirements for *Lantana camara* 'WHITE GOLD' are loam-based soil, full sun, and moderate to regular water.
6. *Lantana camara* 'WHITE GOLD' is propagated by the methods of tip, shoot and internodal cuttings.
7. *Lantana camara* 'WHITE GOLD' is suitable for use in patio containers, planters and borders.
8. *Lantana camara* 'WHITE GOLD' is 45–60 cm. in height and 90–120 cm. in width at maturity.
9. *Lantana camara* 'WHITE GOLD' is hardy to USDA Zone 8.
10. *Lantana camara* 'WHITE GOLD' has not produced seed nor fruit to date and is presumed sterile.

BRIEF DESCRIPTION OF THE DRAWINGS

The accompanying color drawings labeled

Figure 1:
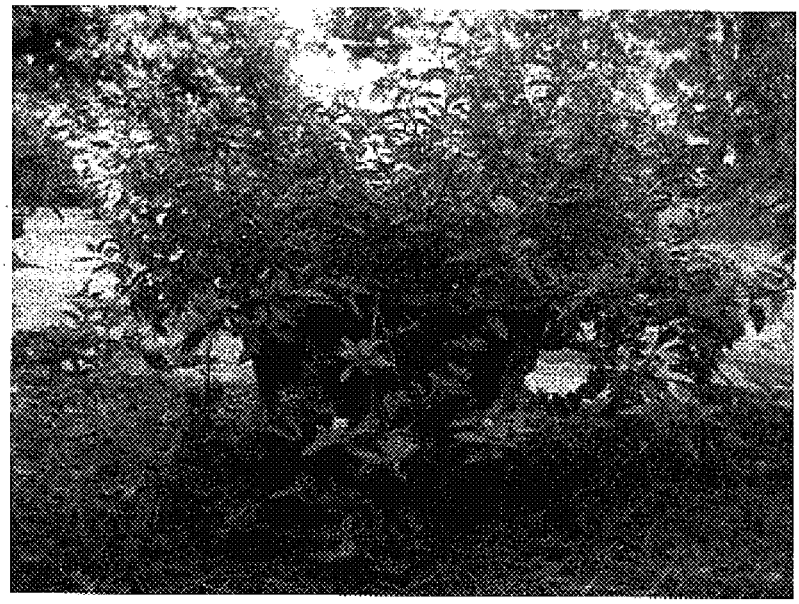
FIG. 1 to FIG. 6 illustrate the overall appearance of the new *Lantana* cultivar 'WHITE GOLD', and including comparative illustrations of the parent variety *Lantana* 'New Gold' and also the variety *Lantana* 'Silver Mound' which the inventor considers most closely resembles 'WHITE GOLD'. The colors depicted are as true as it is reasonably possible to obtain in colored reproductions of this type. Colors in drawings labeled FIG. 1 to FIG. 6 may differ from the color values cited in the detailed botanical description, which accurately describes the actual colors of the new variety 'WHITE GOLD'.

The drawing labeled as FIG. 1 illustrates an entire plant of 'WHITE GOLD' in a 10 inch diameter stock pot. The illustrated plant is approximately four months old having been started as a cutting in January and been grown out-of-doors under partial shade, in Newnan, Ga., USA.

Figure 2:
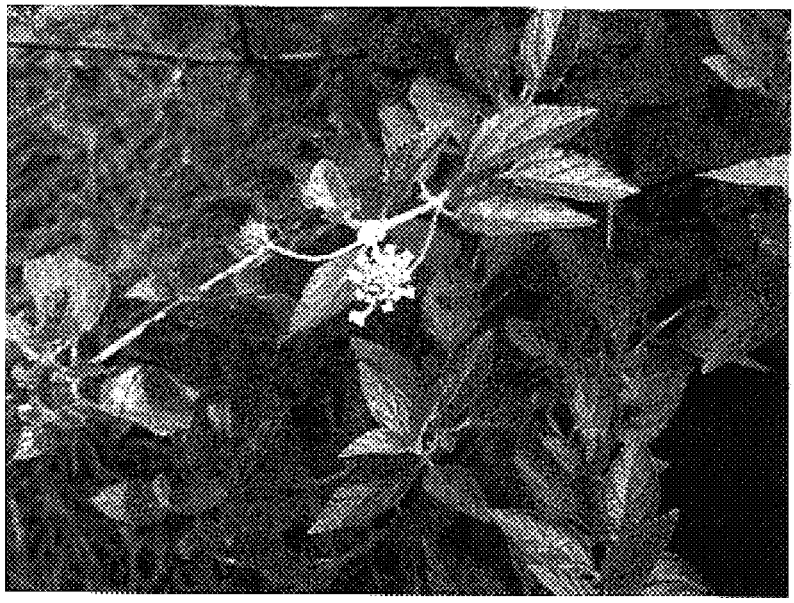

The drawing labeled as FIG. 2 presents a close-up view of the foliage and first inflorescence of the four months old plant in FIG. 1.

Figure 3:
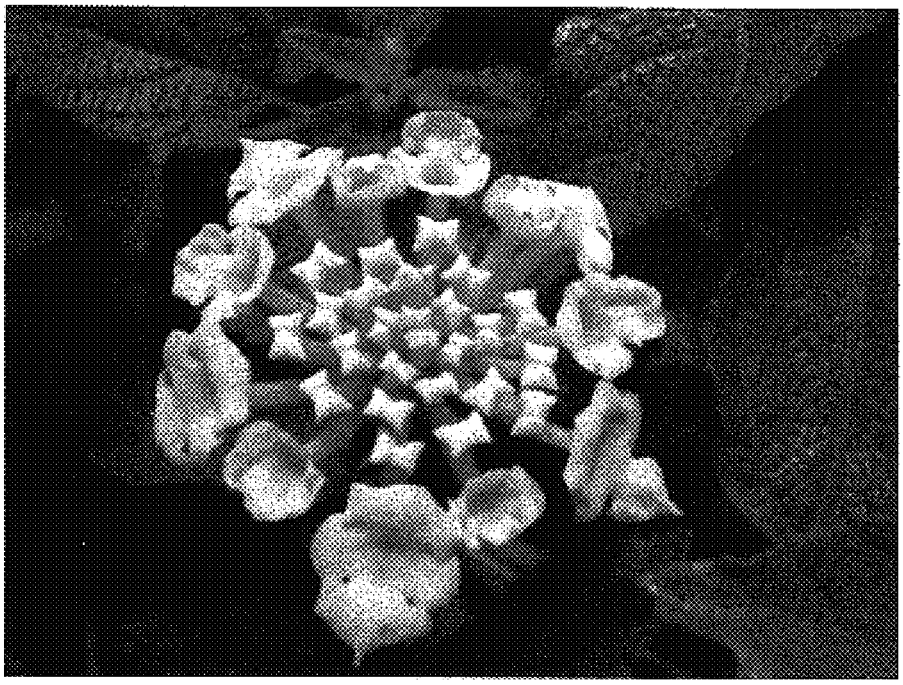

The drawing labeled as FIG. 3 presents a close-up view showing the pale yellow buds and the clear white corolla of the newly-opening inflorescence.

Figure 4:
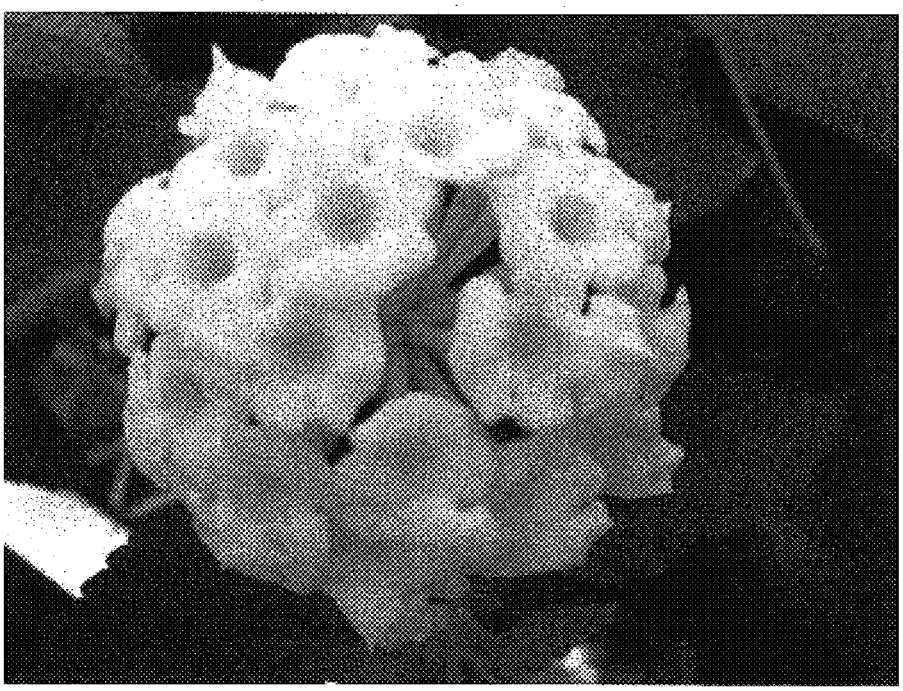

The drawing labeled as FIG. 4 presents a close-up view of a fully developed inflorescence of 'WHITE GOLD' with its uniformly clear white corollas.

Figure 5:
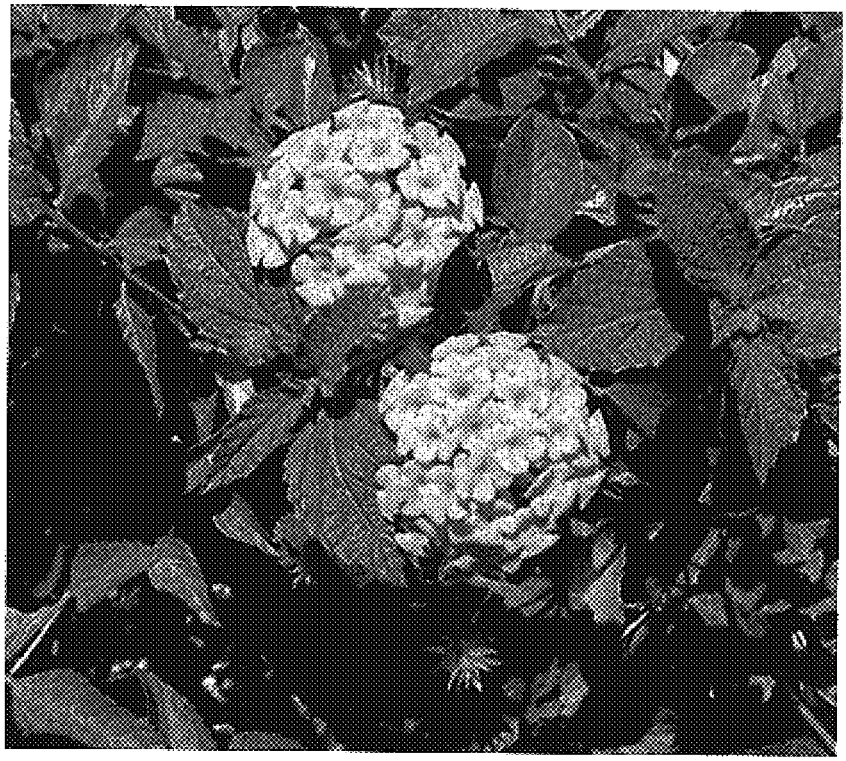

The drawing labeled as FIG. 5 illustrates the inflorescences of the parent variety, *Lantana* 'New Gold' whose corollas are yellow-orange in color.

Figure 6:
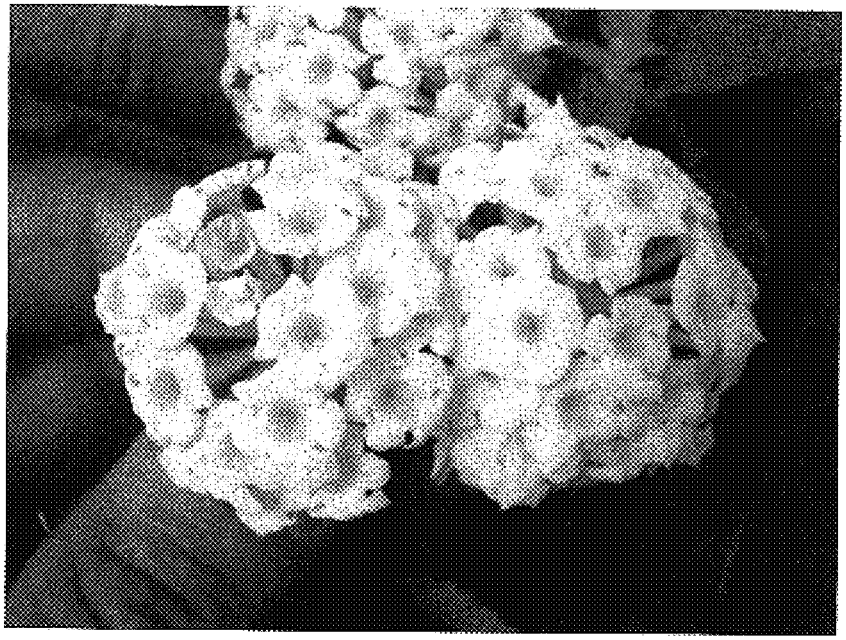

The drawing labeled as FIG. 6 illustrates the comparison between 'WHITE GOLD' which is presented on the right and on the upper center of the drawing, and the variety *Lantana* 'Silver Mound' which is presented on the left of the drawing. The clearer white coloration of the corollas of 'WHITE GOLD' is shown in relation to the pale creamy-yellow coloration of the corollas of *Lantana* 'Silver Mound'.

BOTANICAL DESCRIPTION OF THE PLANT

The following is a detailed description of the new *Lantana* cultivar 'WHITE GOLD' as grown in 25-centimeter containers out-of-doors in Arroyo Grande, Calif. The color determinations are in accordance with the 2001 edition of The Royal Horticultural Society Colour Chart, London, England, except where general color terms of ordinary dictionary significance are used. The color values were determined in April 2005. The readings were taken between 12 p.m. and 3:00 p.m. under natural day light conditions.

Botanical classification: *Lantana camara* 'WHITE GOLD'.
Genus: *Lantana.*
Species: *camara.*
Denomination: WHITE GOLD.
Common name: *Lantana.*
Commercial classification: Perennial.
Plant use: Suitable for use in patio containers, planters or borders.
Suggested container sizes: 'WHITE GOLD' may be produced and finished as a flowering plant in 9 cm to 25 cm diameter containers.
Cultural requirements: Plant in loam-based soil with full sun whilst maintaining adequate moisture at all times. Stems become brittle in conditions of full sun and drought. Vigor: Vigorous.
Root system: Fine and fibrous.
Parentage: *Lantana camara* 'WHITE GOLD' is a naturally occurring branch sport of the following parent:
*Parent plant.*—An individual *Lantana camara* 'New Gold'.
Plant dimensions: 45–60 cm. in height and 90–120 cm. in width at maturity.
Bloom period: Spring through fall.
Plant habit: Mounding spreading habit.
Hardiness: Hardy to USDA Zone 8.
Propagation: Propagation is accomplished by the methods of tip, shoot, and internodal cuttings.

Time to develop roots: 5 days during summer and 7 days during winter are needed for initial cuttings to produce roots.

Air and potting mix temperatures recommended for rooting: Air temperatures of 18–20° Centigrade and potting mix temperature of 21° Centigrade are recommended.

Recommended potting mix and rooting conditions: Propagate and grow in soil-less potting mix under intermittent mist.

Cropping time: Approximately 4–6 weeks to produce a finished 9 cm commercial container plant and 8–10 weeks to produce a finished 13 cm commercial container plant.

Pest and disease resistance and susceptibility: No particular resistance or susceptibility to any pest or disease has been observed.

Stem:

*Stem shape.*—Quadrilateral.
*Stem color.*—144B.
*Stem dimensions.*—12 cm. in length and 3 mm. in diameter.
*Stem surface.*—Hispid.
*Stem texture.*—Bristled.
*Branching.*—Freely branching from base.

Foliage:

*Foliage type.*—Evergreen.
*Leaf arrangement.*—A combination of opposite and whorled on an individual stem.
*Internode length.*—2.5 cm–4.5 cm. between nodes.
*Leaf shape.*—Ovate.
*Leaf margins.*—Crenate.
*Leaf division.*—Simple.
*Leaf venation (adaxial and abaxial surfaces).*—Pinnate.
*Vein color (adaxial surface).*—137A.
*Vein color (abaxial surface).*—138A.
*Leaf surfaces (adaxial and abaxial).*—Hispid.
*Leaf texture.*—Bristled.
*Leaf appearance (adaxial and abaxial surfaces).*—Slightly rugose.
*Leaf width.*—Leaves range from 1.50 cm. to 2.25 cm. in width on an individual plant.
*Leaf length.*—Leaves range from 3 cm. to 4.50 cm. in length on an individual plant.
*Leaf color (adaxial surface).*—137A.
*Leaf color (abaxial surface).*—138A.
*Average number of leaves per stem.*—An average of 28 leaves per individual stem.
*Leaf attachment.*—Petiolate.
*Petiole color.*—144B.
*Petiole surface.*—Hispid.
*Petiole shape.*—Slightly sulcate.
*Petiole dimensions.*—5 mm. in length and 1 mm. in width.
*Stipules.*—Present.
*Stipule shape.*—Oval.
*Stipule color.*—144B.
*Stipule surface.*—Hispid.
*Stipule dimensions.*—2 mm. in length and 0.50 mm. in diameter.
*Leaf fragrance.*—Pungently malodorous when bruised.

Inflorescences:

*Flowering months.*—April through November in California.
*Lastingness.*—A range of 7–8 days.
*Flowering habit.*—Freely flowering.
*Inflorescence type.*—Rounded umbel.
*Inflorescence shape.*—Spherical.
*Inflorescence dimensions.*—4 cm. in diameter and 2 cm. in depth.
*Persistent or self-cleaning.*—Self-cleaning.
*Number of inflorescences per plant.*—A single mature plant towards the end of summer flowering carries approximately 50–100 open flowers and a similar number of buds.
*Quantity of florets per inflorescence.*—An average of 17–20 florets per inflorescence.
*Floret color.*—Colors 155B and 9B are individually present on an individual open floret.
*Floret aspect.*—Florets face upward and outward.
*Floret shape.*—Salverform.
*Floret dimensions.*—0.75 cm. in diameter and 1.25 cm. in depth.
*Petals.*—Four non-imbricate petals.
*Petal color (adaxial and abaxial surfaces).*—155B.
*Petals fused or unfused.*—Petals are fused.
*Petal margin.*—Entire.
*Petal apex.*—Rounded.
*Petal surfaces (adaxial and abaxial surfaces).*—Glabrous.
*Petal dimensions.*—5.50 mm. in length and 4 mm. in width.
*Corolla tube dimensions.*—10 mm. in depth and 2 mm. in diameter.
*Corolla tube color (inner surface).*—155B.
*Corolla tube color (outer surface).*—155B.
*Eye color.*—9B.
*Bud shape.*—Tetrapterous.
*Bud surface.*—Pubescent.
*Bud color.*—11B.
*Bud apex.*—Truncate.
*Bud dimensions.*—6 mm. in length and 2.5 mm. in width.
*Peduncle shape.*—Quadrilateral.
*Peduncle texture.*—Flexible.
*Peduncle strength.*—Strong.
*Flower fragrance.*—Pungently malodorous.

Reproductive organs:

*Stamens.*—Two rudimentary stamens.
*Stamen color.*—155B.
*Stamen dimensions.*—2 mm. in length and less than 0.25 mm. in diameter.
*Anther dimensions.*—Less than 0.50 mm. in length and less than 0.25 mm. in width.
*Anther color.*—N144B.
*Pollen.*—None observed to date.
*Pistil.*—None observed to date.
*Ovary position.*—None observed to date.

Seed production: Neither seed, nor fruit production has been observed to date.

It is claimed:

1. A new and distinct cultivar of *Lantana* plant named 'WHITE GOLD' as described and illustrated herein.

* * * * *